(12) United States Patent
Adelson et al.

(10) Patent No.: US 9,968,532 B2
(45) Date of Patent: May 15, 2018

(54) APPARATUS AND METHODS FOR CONCEALING VITILIGO

(71) Applicant: Zanderm LLC, West Palm Beach, FL (US)

(72) Inventors: James R. Adelson, Far Rockaway, NY (US); Sara R. Frankel, Monsey, NY (US)

(73) Assignee: Zanderm LLC, West Palm Beach, FL (US)

( * ) Notice: Subject to any disclaimer, the term of this patent is extended or adjusted under 35 U.S.C. 154(b) by 0 days. days.

(21) Appl. No.: 14/143,082

(22) Filed: Dec. 30, 2013

(65) Prior Publication Data

US 2014/0369945 A1  Dec. 18, 2014

Related U.S. Application Data

(60) Provisional application No. 61/834,006, filed on Jun. 12, 2013.

(51) Int. Cl.
*A61K 8/35* (2006.01)
*A61Q 19/04* (2006.01)
*A45D 34/04* (2006.01)

(52) U.S. Cl.
CPC .............. *A61K 8/35* (2013.01); *A61Q 19/04* (2013.01); *A45D 34/042* (2013.01); *A45D 34/045* (2013.01); *A45D 2200/057* (2013.01); *A61K 2800/872* (2013.01); *Y10T 29/49826* (2015.01)

(58) Field of Classification Search
CPC ...................................................... A61K 8/35
See application file for complete search history.

(56) References Cited

U.S. PATENT DOCUMENTS

| 4,620,648 | A | 11/1986 | Schwartzman |
| 4,693,623 | A | 9/1987 | Schwartzman |
| 5,612,324 | A | 3/1997 | Guang Lin et al. |
| 6,231,837 | B1 | 5/2001 | Stroud et al. |
| 6,379,069 | B1 | 4/2002 | May |
| 6,561,713 | B2 | 5/2003 | Sukhna et al. |
| 6,641,319 | B2 | 11/2003 | May |
| 6,691,716 | B2 | 2/2004 | Neuner et al. |
| 6,869,242 | B2 | 3/2005 | May |
| 6,883,995 | B1 | 4/2005 | Gueret |
| 6,932,532 | B2 | 8/2005 | Schwartzman et al. |
| 8,406,499 | B2 | 3/2013 | Dobbs |
| 2001/0019682 | A1* | 9/2001 | Sukhna et al. ................ 401/198 |
| 2003/0003065 | A1 | 1/2003 | Kalla et al. |

(Continued)

FOREIGN PATENT DOCUMENTS

WO   WO1998051263   11/1998

OTHER PUBLICATIONS

"Tanee Tan Line Corrector," Tanee, Retrieved on Jun. 3, 2013.
(Continued)

*Primary Examiner* — Benjamin Packard
(74) *Attorney, Agent, or Firm* — Weiss & Arons LLP

(57) ABSTRACT

A method for concealing vitiligo is provided. The method comprises depressing a spring head. The spring head may be covered by a covering. Depression of the spring head may saturate the covering with a solution. The solution may include a bronzer and dihydroxyacetone ("DHA"). The method may also comprise guiding the saturated covering over a portion of depigmented skin.

10 Claims, 8 Drawing Sheets

(56) References Cited

U.S. PATENT DOCUMENTS

| | | | |
|---|---|---|---|
| 2007/0041917 A1 | 2/2007 | Thomas | |
| 2007/0292459 A1 | 12/2007 | Cooper et al. | |
| 2008/0152680 A1* | 6/2008 | Brown et al. | 424/401 |
| 2009/0206174 A1 | 8/2009 | Arnaud et al. | |
| 2010/0322983 A1 | 12/2010 | Griffiths-Brophy et al. | |
| 2011/0137268 A1 | 6/2011 | Thomason et al. | |

OTHER PUBLICATIONS

"Plastic Ampoules," James Alexander Corporation, Jan. 31, 2011.
"Unit Dose Swabs," James Alexander Corporation, Retrieved on May 23, 2013.
"Plastic Ampoule Technical Data Sheet," James Alexander Corporation, Retrieved on May 23, 2013.
"Norvell—Tan Perfect Pen," Norvell Skin Solutions, LLC., Retrieved on May 29, 2013.
"Receive New Norvell Tan Perfect Pen," EYE PRO, Oct. 1, 2011.
"Norvell Tan Perfect Pen 2ml," Folica.com, Retrieved on May 29, 2013.
"Nowell Tan Perfect Pen—Touch up Pen," TanningLotionSupply. com, Retrieved on May 29, 2013.
"Sunless Tanning," Wikipedia.org, May 25, 2013.
"Tattoo Markers," Dri Mark Products Inc., Retrieved on May 29, 2013.
"Specialty Ink / Manufacturing," Dri Mark Products Inc., Mar. 6, 2011.
Hoffman, Jon, "Inventing Success—Tanee Tanline Corrector (video transcribed)," May 23, 2012.
International Search Repot for International Application No. PCT/US14/42133, International Searching Authority, dated Dec. 2, 2014.
Written Opinion for International Application No. PCT/US14/42133, International Searching Authority, dated Dec. 2, 2014.
Invitation to Pay Additional Fees, And, Where Applicable, Protest Fee for International Application No. PCT/US14/42133, International Searching Authority, dated Sep. 9, 2014.
Invitation to Pay Additional Fees, And, Where Applicable, Protest Fee for International Application No. PCT/US15/20097, International Searching Authority, dated May 11, 2015.
"Vitiligo," Wikipedia.org, Nov. 4, 2013.
"Caps and Applicators," Dab-O-Matic.com, 2009.
"Tips on using Sunless or Self Tanners," VitiligoSupport.org, 2009.
"Camouflaging vitiligo with sunless tanning products," Love2bTanned.com, Jun. 22, 2011.
"Patient Comments: Vitiligo—Effective Treatments," MedicineNet.com, Nov. 13, 2013.
International Search Report for International Application No. PCT/US15/20097, International Searching Authority, dated Jul. 14, 2015.
Written Opinion of the International Searching Authority for International Application No. PCT/US15/20097, International Searching Authority, dated Jul. 14, 2015.
"Dab-O-Matic Sample Box," Dab-O-Matic, Mt. Vernon, New York, Nov. 14, 2013.

* cited by examiner

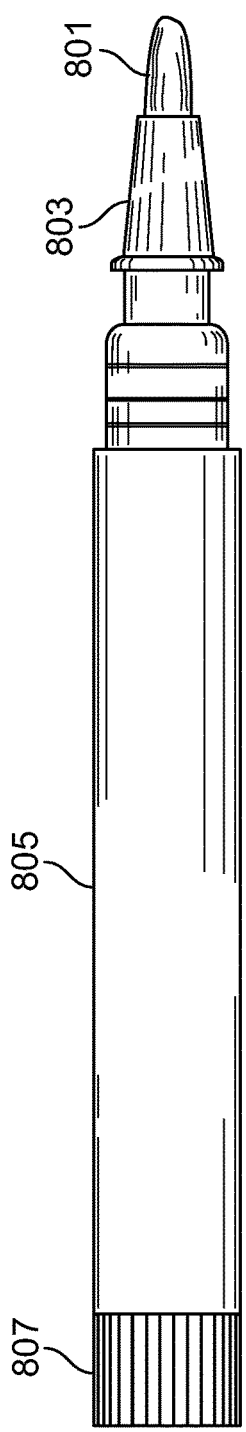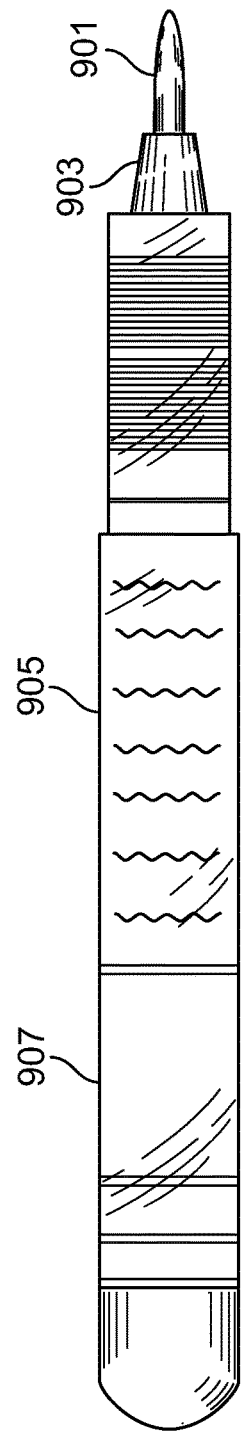

APPARATUS AND METHODS FOR CONCEALING VITILIGO

CROSS-REFERENCE TO RELATED APPLICATION

This application claims the benefit of U.S. Provisional Application No. 61/834,006, filed on Jun. 12, 2013, which is hereby incorporated by reference herein in its entirety.

FIELD OF TECHNOLOGY

This invention relates to a method for concealing vitiligo. More specifically, this invention relates to a method for concealing vitiligo that includes using an applicator to accurately apply a camouflaging solution onto a portion of skin affected by vitiligo.

BACKGROUND OF THE DISCLOSURE

Vitiligo is a condition that causes skin depigmentation on portions of a human body. Vitiligo depigmentation typically occurs on the extremities of the body, such as the face, mouth, eyes, nostrils, hands and feet. Typically, the depigmentation is manifest in patches that cover small or large areas of the body.

Skin depigmentation from vitiligo is caused by the death of skin cells responsible for skin pigmentation. The skin cell death creates a completely white area on an area of skin which was previously pigmented.

Because vitiligo completely depigments the skin, there is a stark contrast between the white, depigmented skin, and the surrounding pigmented skin. As a result, these symptoms are visible to onlookers when the affected area is exposed.

Current methods used to treat vitiligo include phototherapy, immune mediators, complete skin-depigmentation and/or melanocyte transplantation. These methods are intrusive because they include medications, steroids, surgery, and/or exposure to phototherapy.

Other methods are available to conceal vitiligo, and do not treat underlying cause of the disease. For example, methods for concealing vitiligo include using creams or makeup to camouflage the depigmented skin. The camouflaging effect of these creams and makeup typically lasts anywhere from 6-12 hours. Thus, the camouflaging effect is temporary and can be easily removed.

It would be desirable, therefore, to provide a method for camouflaging vitiligo symptoms that both conceals the depigmented skin and lasts substantially longer than 6-12 hours.

In addition, application of such a solution to a depigmented area of skin must be carefully and precisely applied. Therefore, an applicator for applying a solution to a depigmented area must be easy to control, and dispense a predictable amount of solution. This is because the application of more or less solution could result in overly darkened skin or pigmenting skin that is naturally pigmented. This could result in uneven coloring of the body and stain clothing as well, rendering the applicator unsuitable for its intended purpose of creating a uniform coloring on the body.

It would be desirable, therefore, to provide a method for camouflaging vitiligo that includes using an applicator that precisely and uniformly applies a camouflaging solution to depigmented skin.

SUMMARY OF THE DISCLOSURE

Apparatus and methods for concealing vitiligo are provided. The method may include guiding a nib along a portion of depigmented skin. The nib may be formed from resin and saturated with a solution. The solution may comprise a bronzer and dihydroxyacetone ("DHA"). The nib may be saturated with the solution by capillary action from a fibrous reservoir.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 8 shows illustrative apparatus for use with the systems and methods of the invention;

FIG. 9 shows illustrative apparatus for use with the systems and methods of the invention;

DETAILED DESCRIPTION OF THE DISCLOSURE

Figure 1:
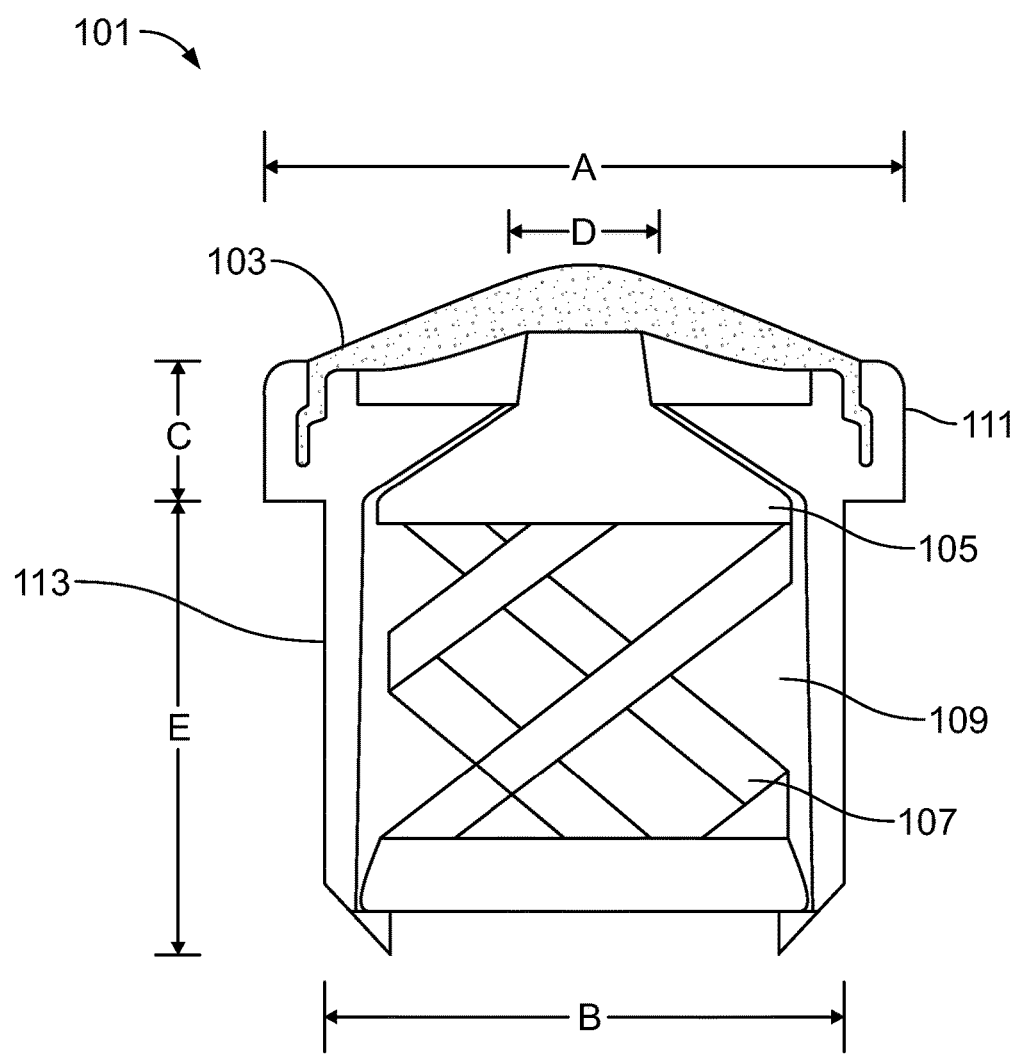
FIG. 1 shows illustrative apparatus for use with the systems and methods of the invention.

Apparatus for an applicator configured to accurately apply a solution for concealing vitiligo is provided. In some embodiments, the applicator may be a marker-like applicator, a spring-tension applicator, or any other suitable applicator.

Solution for Concealing Vitiligo

The solution for concealing vitiligo (hereinafter, 'the solution') may include a bronzer, a sunless tanner and/or any other suitable ingredient(s).

Any suitable bronzer may be may be included in the solution. For the purposes of the application, a bronzer may be any combination of natural and/or unnatural ingredients that changes the color of the skin. For example, the bronzer may give the skin a darker look, a tanned look, or any other different appearance. In some embodiments, the bronzer may be an all-natural bronzer. Additionally or alternatively, the bronzer may be an instant bronzer.

The bronzer included in the solution may affect the immediate coloring of the depigmented skin area. Thus, the bronzer may be used to initially camouflage the dipigmented skin. It should be note that in addition to, or instead of, the bronzer, the solution may include any other suitable ingredient(s) that color the skin.

Any suitable sunless tanner may be included in the solution. For the purposes of the application, a sunless tanner may be a product that creates a tanned appearance on the skin without exposing the skin to either the sun or another source of ultraviolet radiation. An exemplary sunless tanner that may be used is dihydroxyacetone ("DHA"). The DHA may be derived from sugar, such as sugar beets or sugar cane, or through any other known process.

In the embodiments that the solution includes the sunless tanner DHA, the DHA may affect a coloring of depigmented skin when applied to an area of depigmented skin. The coloring affected by the DHA may last longer relative to the coloring affected by the bronzer. Application of the DHA may not automatically affect a change in the skin color. However, application of the DHA to the skin may trigger a chemical reaction with amino acids present in the epidermal layer located at the skin's surface. After the passage of time, such as 2-4 hours, the chemical reaction may begin to create a brown color on the upper layer of the skin. The brown color may continue to darken for the next 24-72 hours. The brown color may typically last anywhere from 3 to 10 or more days, depending on how much DHA was applied and the natural exfoliation rate of the skin.

The solution may have high or low viscosity. The solution may take any suitable physical form. For example, the solution may take the physical form of an emulsion, cream, solid, stick, waxy solid, ointment, balm, paste, film and/or a watery liquid.

An exemplary appearance of the solution may be a dark brown liquid, a light brown liquid, any other suitable shade of brown or any other suitable color. The solution may have a fragrance to mask its original odor, such as a Tropical Gold Fragrance or any other suitable fragrance.

An exemplary solution may include one or more of water, deionized water, glycerin, DHA, isopentyldiol, Black Walnut Extract, caramel color, phenoxyethanol, citric acid, fragrance, artificial color(s) such as a brown color, one or more preservatives, natural and/or not natural coloring agent(s), and any other suitable ingredient(s). In some embodiments, the solution may also include one or more of lycopene, the amino acid Tyrosine, the synthetic melatonin-stimulating hormone analog afamelanotide and/or bronzer(s).

In some embodiments, the solution for concealing vitiligo may be substantially similar to a tan line correction solution used to conceal unwanted tan lines.

Application of the solution to an area affected by vitiligo may result in a two step process. The first step may be the immediate camouflage of the skin by the bronzer. The second step may be the browning of the skin resultant from the chemical reaction triggered by the DHA.

Thus, the application of the solution may camouflage, blend, cover, disguise, and/or conceal the depigmented area of skin, resulting in a more homogenous appearance of the skin. The camouflaging, blending, covering, disguising, and/or concealing of the depigmented area of skin may last for three to ten, or more, days.

Applicators

The solution may be contained in any suitable applicator. Any applicator known to those skilled in the art may be used to hold the solution. For example, the solution may be contained in a spring-tension applicator, a spray bottle including a pump, a roller-ball bottle, a dispensing tube, a vial with a cap including an applicator, a squeeze bottle, a lipstick-like holder, a jar, a marker, a pen, a cream dispenser, or any other suitable container or cosmetic applicator.

In the embodiments in which the solution is held in a reservoir, the reservoir may be a liquid reservoir, an open reservoir, a fibrous reservoir, or any other suitable reservoir.

Spring-Tension Applicator

In some embodiments, the applicator may be a spring-tension applicator (hereinafter, 'spring applicator'). The spring applicator may be any spring applicator known to those skilled in the art, such as the spring applicator produced by Dab-O-Matic Corp., located in Mount Vernon, N.Y.

In some embodiments, the spring applicator may include an applicator head and an applicator barrel. The applicator head may be inserted into, and supported by, the applicator barrel.

The applicator barrel may be any suitable shape and size. For example, the applicator body may comprise one or more cylindrical, rectangular, oval, substantially circular, and/or any other suitable shape(s). The applicator barrel may be closed at one end and open at the other end. An inner area of the applicator barrel may be hollow. At least a portion of the hollow area of the applicator barrel may be filled with the solution for concealing vitiligo disclosed herein.

The applicator head may be configured to be inserted into, or onto, the open end of the applicator barrel. Insertion of the applicator head into, or onto, the applicator barrel may form a fluid-tight connection. In some embodiments, the applicator head may be screwed onto the barrel, forming a fluid-tight connection. The fluid-tight connection may ensure that the substance cannot leak from the point of connection between the applicator head and the applicator barrel.

In exemplary embodiments, the applicator barrel may be substantially cylindrical. The substantially cylindrical shape of the applicator barrel may include a single diameter or two or more diameters. In some of these embodiments, at least a portion of a first cylindrical shape may be configured to hold the applicator head and at least a portion of a second cylindrical shape may be configured to hold the solution.

In some embodiments, the first cylindrical shape may form a unitary body with the second cylindrical shape. In some embodiments, the first cylindrical shape may be fixedly attached to the second cylindrical shape.

The applicator head may include a cylindrical body and a circular head. The circular head may be located on top of the cylindrical body. In some embodiments, the cylindrical body and the circular head may form a unitary structure. In some embodiments, the cylindrical body may be fixedly attached to the unitary head.

The circular head may have a diameter greater than the diameter of the cylindrical body. In some embodiments, the diameter of the circular head may be equal to a diameter located at the open end of the applicator barrel. In some of these embodiments, insertion of the applicator head into the applicator barrel may position the cylindrical body within the applicator barrel and position the circular head flush on top of the applicator barrel. The top of the circular head may be a substantially solid surface with one or more holes located on the top of the circular head.

The applicator head may include a spring, and a spring head. The spring may be located in a hollow portion of the cylindrical body. The spring head may be located on the top of the spring. When the spring is at rest, the spring may urge at least a portion of the spring head into the one or more holes located at the top of the circular head.

When the spring head is urged into the one or more holes, the spring head may form a fluid tight, or substantially fluid tight, seal. Thus, any solution that is located in the applicator head may be obstructed from leaving the applicator while the spring head is urged into the hole(s).

The spring may be formed from any desirable material, such as one or more of high density polyethylene ("HDPE"), low density polyethylene (LDPE), celcon and/or polypropylene. The spring may be positioned in a hollow inner portion of the cylindrical body.

The top of the circular head may be covered by a covering. The covering may be formed from any desirable material, such as one or more of polyurethane, neoprene, nylon taffeta, mohair, brushed nylon tricot, APL tricot, nylon fleece, compressed polyurethane and/or nylon taffeta over neoprene.

A user of the spring applicator may desire to cover an area of depigmented skin with the solution. The user may bring the covering into physical contact with the depigmented skin and press the covering into the depigmented skin area.

Depression of the covering may depress the spring head located under the covering. Depression of the spring head may depress the spring, moving the spring head downwards in the direction of the cylindrical body. Movement of the spring head downwards may open the holes in the circular head. The opening of the holes in the circular head may allow the solution contained in the applicator barrel to flow through the cylindrical body, through the holes in the circular head, and saturate the covering.

In some embodiments, the applicator barrel may hold the solution in an open reservoir. In some embodiments, the applicator barrel may hold the solution in a fibrous reservoir.

Advantages of the spring applicator in accordance with the principles of the invention include the ability to apply a substantially constant amount of solution to a surface. This obtains precise application of solution. Additionally, the predictability of the solution flow may minimize the problem of leaking and dripping. Furthermore, because the spring head maintains the solution in a sealed environment until the spring is depressed, the solution is less likely to dry out with the passage of time.

Marker-like Applicator

In some embodiments, the applicator may be a marker-like, or pen-like applicator (hereinafter, 'marker applicator'). The marker applicator may be any marker applicator known to those skilled in the art, such as the marker applicator produced by Dri Mark™ Products, Inc., located in Bethpage, N.Y.

In some embodiments, the marker applicator may include a marker barrel, a fibrous reservoir located inside the marker barrel and a nib in fluid communication with the reservoir. The marker applicator may additionally include the solution. The solution may be held in suspension within the fibrous reservoir, or some other suitable reservoir, and delivered by capillary action, through the fibers, to the nib. Movement of the nib along a surface may result in the application of a preferably regulated amount of the solution to the surface. The rate may be regulated at a predetermined rate dependent on the characteristics of the nib and the reservoir.

Exemplary attributes for a solution that may be used in a marker applicator in accordance with the invention are included in Table 1 below.

TABLE 1

| Attribute | Exemplary Ranges | Exemplary Value |
|---|---|---|
| Specific Gravity | 0.95-1.15, 0.90-1.2, 1-1.10 | 1.06 |
| pH | 2.8-3.5, 2.5-3.7, 3-3.3 | 2.85 |
| Viscosity (Spindle # 3/100 RPM/1 min) | 5-20 cps, 7-17 cps, 4-23 cps, 10-15 cps | 14 cps |

The marker applicator may include a marker barrel, a back end plug, a fibrous reservoir, a nib and a cap.

The marker barrel may be formed from glass, aluminum, plastic, or any other suitable material. The marker barrel may include a front end and a back end. The marker barrel may be hollow in the middle and include an open space in one or more of the front end and the back end. In some embodiments, a plug may be inserted in the open space located at the back end of the marker barrel.

The reservoir may be positioned inside the marker barrel. In some embodiments, the reservoir may be inserted into the marker barrel through the open space located at the back end of the marker barrel. For example, a robotic arm may thrust the reservoir into the plastic barrel.

A plug may be subsequently inserted into the open space at the back end of the marker barrel, holding the reservoir in place.

The shape of the reservoir may be the same as, or substantially similar to, an elongated cylinder, an elongated rectangle, or any other suitable geometric shape. The reservoir may comprise a shell filled with a porous, absorbent and/or fibrous filling. The shell may be described herein as having a tubular shape. However, it should be noted that the shell may have any other suitable shape, such as a rectangular shape or any other suitable geometric shape.

Some embodiments may include a porous, absorbent and/or fibrous reservoir without a shell.

In some embodiments, the tubular shell may be formed from non-rigid material. In other embodiments, the tubular shell may be formed from rigid material.

The tubular shell may be filled with a filling. The filling may be densely packed in the tubular shell. The filling may be made from felt and/or polyester. Exemplary polyester included in the tubular shell includes a densely packed highly porous polyester fiber. In some embodiments, the filling may include a set of tubes wrapped in plastic.

The filling included in the reservoir may be saturated with the solution. The filling may retain the solution in suspension.

In some embodiments, a vacuum pump may suck the solution into needles. Each needle may be then be pushed by a robotic arm into a reservoir and inject the solution into the filling, saturating the filling with the solution.

The flow of solution in the reservoir may be anisotropic. In other words, the flow of the solution in the reservoir may have a directional preference. The directional preference may be along the longitudinal axis of the marker barrel.

A nib may be inserted through the open space located at the forward end of the marker barrel. For example, in some embodiments, the nib may be pushed into the open space at the forward end of the marker and held in place by a tension fit. This may also bring the nib into physical contact with the reservoir.

In exemplary embodiments, mechanical vibration and/or pressed air may drive a conveyer belt carrying nibs. The nibs may fall into the clutch of a mechanical claw. The mechanical claw may drop the nibs onto a circular pusher. A circular pusher may force each nib into a marker barrel. The force from the pusher may cause the nib and the marker barrel to interlock, and to bring the nib into physical contact with the reservoir.

The impact between the nib and the reservoir resultant from the insertion of the nib into the marker barrel may flood the nib with solution retained in the reservoir. In some embodiments, the reservoir may deliver the solution to the nib through capillary action. In some embodiments, the force of gravity may also assist in delivering solution from the fibrous reservoir to the nib.

The nib may be porous, oriented and/or include many channels. Exemplary material used to form the nib includes pressed fibers, resin, plastic, polyester, acrylic and/or porous polyethylene. For example, the nib may be formed from highly-porous, oriented, polyester fiber. The physical composition of the nib may assist the nib in absorbing solution from the reservoir by capillary action.

In some embodiments, the nib may be relatively dense and retain its shape when depressed on a surface. It should be noted that the nib may be substantially denser than laminated polyester foam.

The viscosity of the solution may be matched up with the porosity of the nib and the density of the fibrous filler. This matching may be used to ensure that the solution works in an optimal capillary reaction with the nib and the fibrous filler.

The nib may be held in a stationary position on the marker barrel. Alternatively, the nib may be retractable.

Movement of the nib along a surface may result in the nib dispensing solution on the surface. The amount of solution dispensed by the nib may be substantially constant. In some embodiments, a user may not be able to adjust the amount of solution being dispensed from the nib. In other embodiments, a user may be able to adjust the amount of solution being dispensed from the nib. Such adjustment may be accomplished using methods that are known in the art.

The marker barrel may also include a cap. The cap may be removably secured to the forward end of the marker barrel. The cap may protect the nib from being deformed and/or drying out.

Advantages of the marker applicator in accordance with the principles of the invention include the ability to apply a substantially constant amount of solution to a surface. This results in the precise application of solution, because of the predictability of the solution flow. Additionally, the nib of the marker applicator in accordance with the invention retains the solution in a manner that eliminates the problem of leaking and dripping.

Figures

Illustrative embodiments of apparatus and methods in accordance with the principles of the invention will now be described with reference to the accompanying drawings, which form a part hereof It is to be understood that other embodiments may be utilized and structural, functional and procedural modifications may be made without departing from the scope and spirit of the present invention.

FIG. 1 illustrates exemplary applicator head 101. Exemplary applicator head 101 may include circular head 111 and cylindrical body 113.

Cylindrical body 113 may enclose hollow area 109. Hollow area 109 may be in fluid communication with an applicator barrel (not shown). Thus, solution held in the applicator barrel may flow freely between the applicator barrel and hollow area 109.

Circular head 111 may be covered by covering 103. Circular head may have an opening with a diameter D.

Spring head 105 may be attached to spring 107. Spring head may include a top portion and a bottom portion. The top portion may cylindrical or substantially cylindrical. The bottom portion may be a frustoconical shape. Spring 107 may be positioned in cylindrical body 113. When spring 107 is at rest, spring 107 may urge spring head 105 into open area D.

The urging of spring head 105 into open area D may position the top portion of spring head 105 against open area D, creating a fluid-tight, or substantially fluid-tight, seal around open area D. The urging of spring head 105 may also position the bottom portion of spring head 105 flush against a portion of open space 119. The positioning of the bottom portion of spring head 105 flush against a portion of open space 119 may create an additional fluid-tight, or substantially fluid-tight, seal. The creation of the fluid-tight, or substantially fluid-tight, seals may obstruct the flow of any fluid located in hollow area 109 through open area D.

Depression of covering 103 may in turn depress spring head 105. Spring head 105, when depressed, may move downward relative to open area D, compressing spring 107.

Spring head 105 may have diameter G. Hollow area 109 may have diameter B'. Diameter B' may be larger than diameter G. Thus, the depression of spring head 105 may create fluid communication between hollow area 109 and covering 103. In the event that solution is retained in hollow area 109, fluid communication between hollow area 109 and covering 103 may result in the saturation of covering 103 with solution.

In some embodiments, circular head may have height C and diameter A. In some embodiments, cylindrical body 113 may have height E and diameter B. Additionally, in some embodiments, a spring applicator in accordance with the invention may include a min./max. container neck measurement F.

Exemplary measurements for dimensions A, B, C, D, E and F, in inches, are included in Table 2 and Table 3 below. It should be noted that measurements included in Table 2 and Table 3 below are for illustrative purposes only. Any suitable measurements may be used for a spring applicator in accordance with the invention.

TABLE 2

| Dimension | Example 1 | Example 2 | Example 3 | Example 4 |
|---|---|---|---|---|
| A | .385 | .515 | .600 | .600 |
| B | .297 | .415 | .425 | .485 |
| C | .165 | .165 | .170 | .170 |
| D | .165 | .200 | .210 | .210 |
| E | .370 | .485 | .485 | .485 |
| F | .270/.284 | .390/.405 | .400/.415 | .460/.475 |

TABLE 3

| Dimension | Example 5 | Example 6 | Example 7 | Example 8 |
|---|---|---|---|---|
| A | .850 | .850 | .980 | 1.135 |
| B | .650 | .710 | .725 | .820 |
| C | .175 | .175 | .175 | .200 |
| D | .250 | .250 | .320 | .250 |
| E | .515 | .515 | .585 | .515 |
| F | .625/.640 | .685/.700 | .695/.715 | .790/.810 |

Figure 2A:
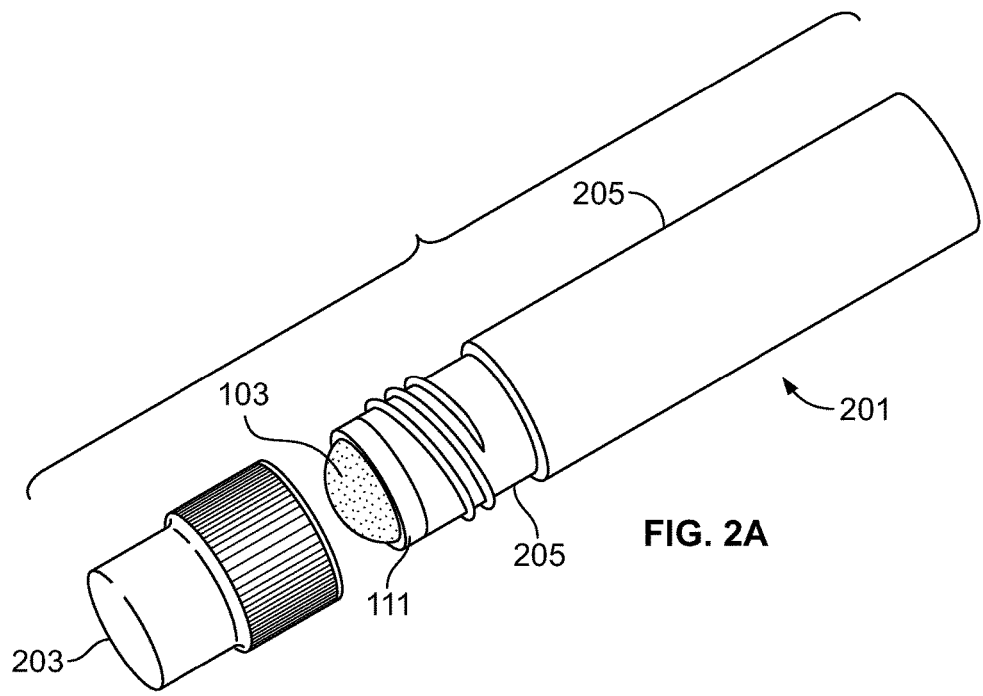
FIGS. 2A-2B shows illustrative apparatus for use with the systems and methods of the invention.

FIG. 2A illustrates spring applicator 201 for use with the principles of the invention. Spring applicator 201 includes applicator barrel 205, applicator head 111 inserted into applicator barrel 205, and covering 103 located on top of applicator head 111. Cap 203 is also illustrated in FIG. 2A. Cap 203 is configured to be removably attached to applicator barrel 205.

Figure 2B:
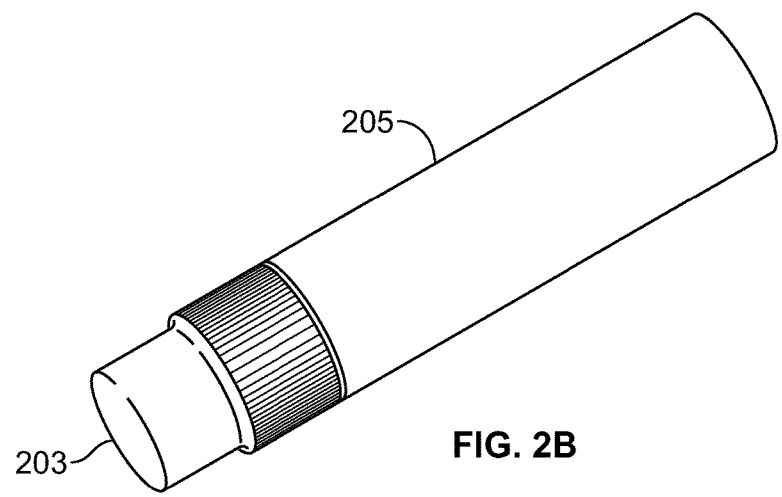

FIG. 2B illustrates a cap 203 removably attached to applicator barrel 205.

Figure 3:
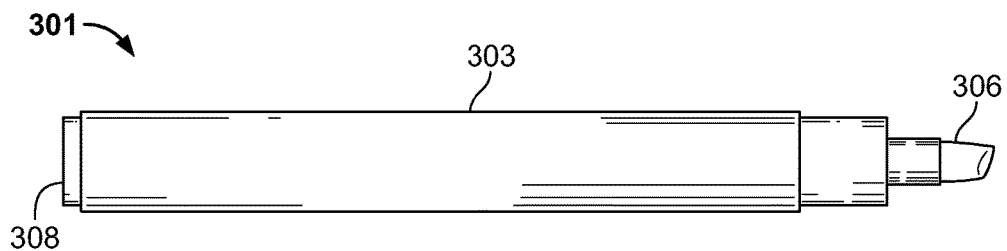
FIG. 3 shows illustrative apparatus for use with the systems and methods of the invention.

FIG. 3 illustrates marker applicator 301 for use with the principles of the invention. The marker applicator illustrated in FIG. 3 includes marker barrel 303, nib 306 and plug 308.

Figure 4:
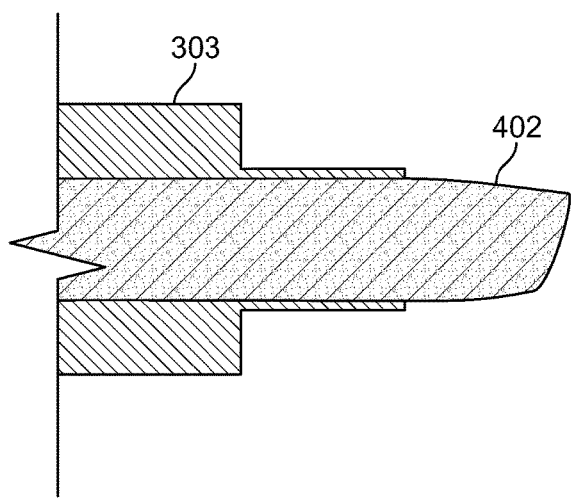
FIG. 4 shows illustrative apparatus for use with the systems and methods of the invention.

FIG. 4 illustrates a portion of a marker applicator for use with the principles of the invention. FIG. 4 illustrates nib 402 inserted into marker barrel 303.

Figure 5:
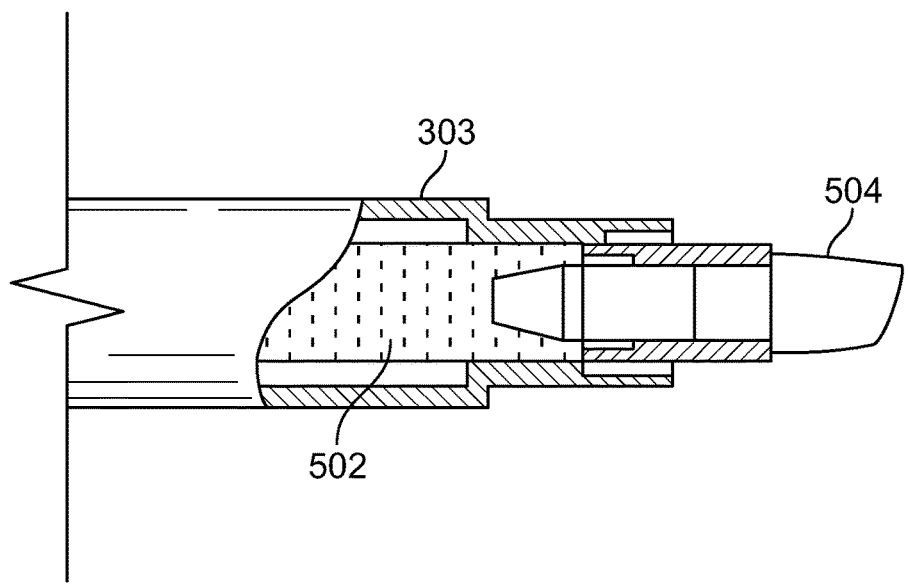
FIG. 5 shows illustrative apparatus for use with the systems and methods of the invention.

FIG. 5 illustrates another portion of a marker applicator for use with the principles of the invention. FIG. 5 illustrates nib 504 inserted into marker barrel 303. Nib 504 is preferably in physical contact, and fluid communication, with reservoir 502.

Reservoir 502 may be saturated with solution. Reservoir 502 may hold the solution in suspension. Reservoir 502 may the solution to nib 504 by capillary action.

Figure 6:
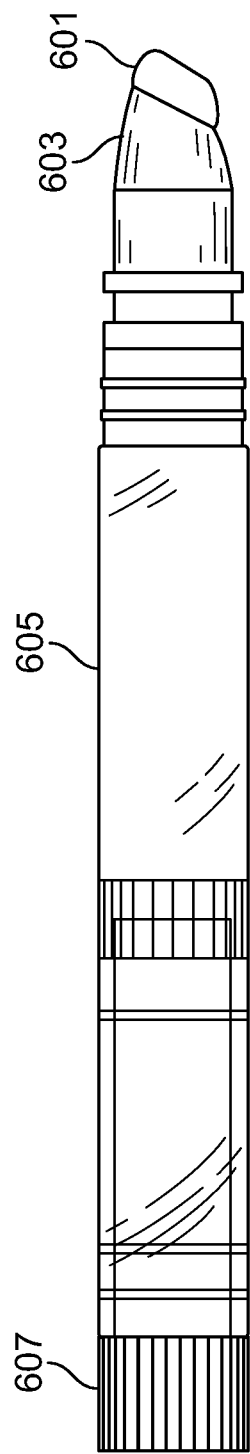
FIG. 6 shows illustrative apparatus for use with the systems and methods of the invention.

FIG. 6 illustrates another applicator for use with the invention. The applicator illustrated in FIG. 6 may include applicator tip 601 and head 603. Applicator tip 601 may be supported by head 603. The applicator may additionally include body 605. Body 605 may include a reservoir that holds the solution in accordance with the invention. The applicator may further include rotatable end 607. Rotatable end 607, when rotated, may dispense solution from the reservoir into applicator tip 601.

Figure 7:
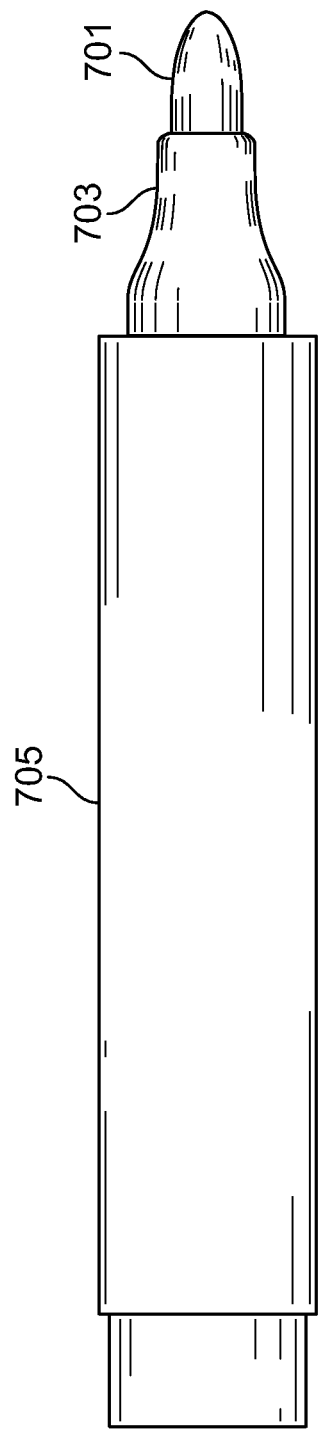
FIG. 7 shows illustrative apparatus for use with the systems and methods of the invention.

FIG. 7 illustrates yet another applicator for use with the invention. The applicator illustrated in FIG. 7 may include applicator tip 701 and head 703. Applicator tip 701 may be supported by head 703. The applicator may also include body 705. Body 705 may include a reservoir that holds the solution in accordance with the invention.

FIG. 8 illustrates yet another applicator for use with the invention. The applicator illustrated in FIG. 8 may include applicator tip 801 and head 803. Applicator tip 801 may be supported by head 803. The applicator may also include body 805. Body 805 may include a reservoir that holds the solution in accordance with the invention. The applicator may additionally include rotatable end 807. Rotatable end 807, when rotated, may dispense solution from the reservoir into applicator tip 801.

FIG. 9 illustrates yet another applicator for use with the invention. The applicator illustrated in FIG. 9 may include applicator tip 901 and head 903. Applicator tip 901 may be supported by head 903. The applicator may also include body 905. Body 905 may include a reservoir that holds the solution in accordance with the invention. The applicator may additionally include end portion 907. End portion 907 may form a portion of the applicator that does not hold solution in accordance with the invention.

Figures 10, 11:
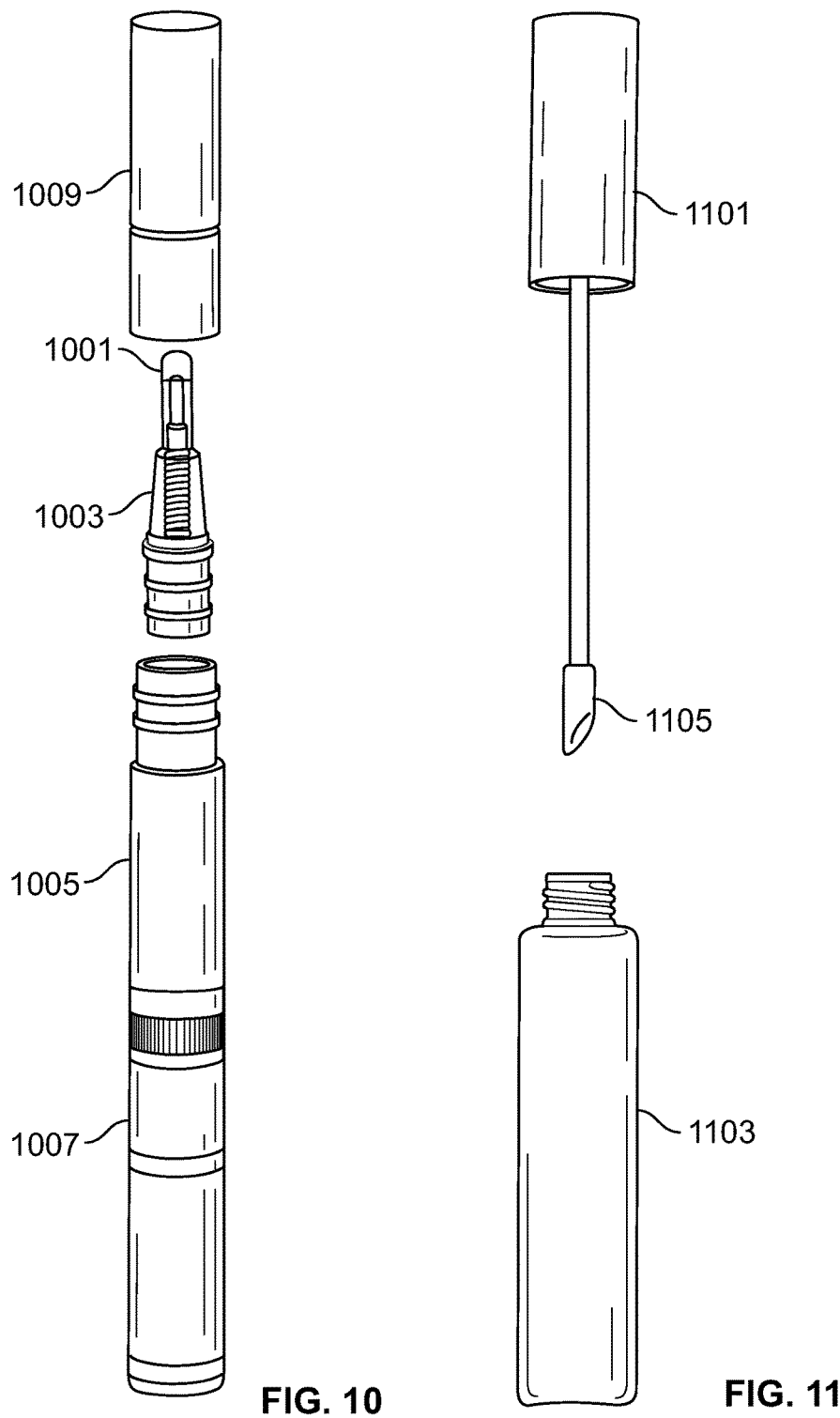
FIG. 10 shows illustrative apparatus for use with the systems and methods of the invention.
FIG. 11 shows illustrative apparatus for use with the systems and methods of the invention.

FIG. 10 illustrates yet another applicator for use with the invention. The applicator illustrated in FIG. 10 may include applicator tip 1001 and applicator head 1003. Applicator tip 1001 may be supported by applicator head 1003. Applicator head may fit into body 1005. Body 1005 may include a reservoir that holds solution in accordance with the invention. The applicator may also include end portion 1007. End portion 1007 may form a portion of the applicator that does not hold solution. The applicator may additionally include cap 1009.

In some embodiments, end portion 1007 may be rotated around body 1005. Rotation of end portion 1007 around body 1005 may dispense solution from the reservoir to applicator tip 1001.

FIG. 11 illustrates yet another applicator for use with the invention. The applicator illustrated in FIG. 11 may include vial 1003. Vial 1003 may hold solution in accordance with the invention. The applicator may also include cap 1101. Cap 1101 may screw onto vial 1003. Cap 1101 may include tip 1105. Tip 1105 may be fixedly or removably attached to cap 1101.

Figures 12, 13, 14:
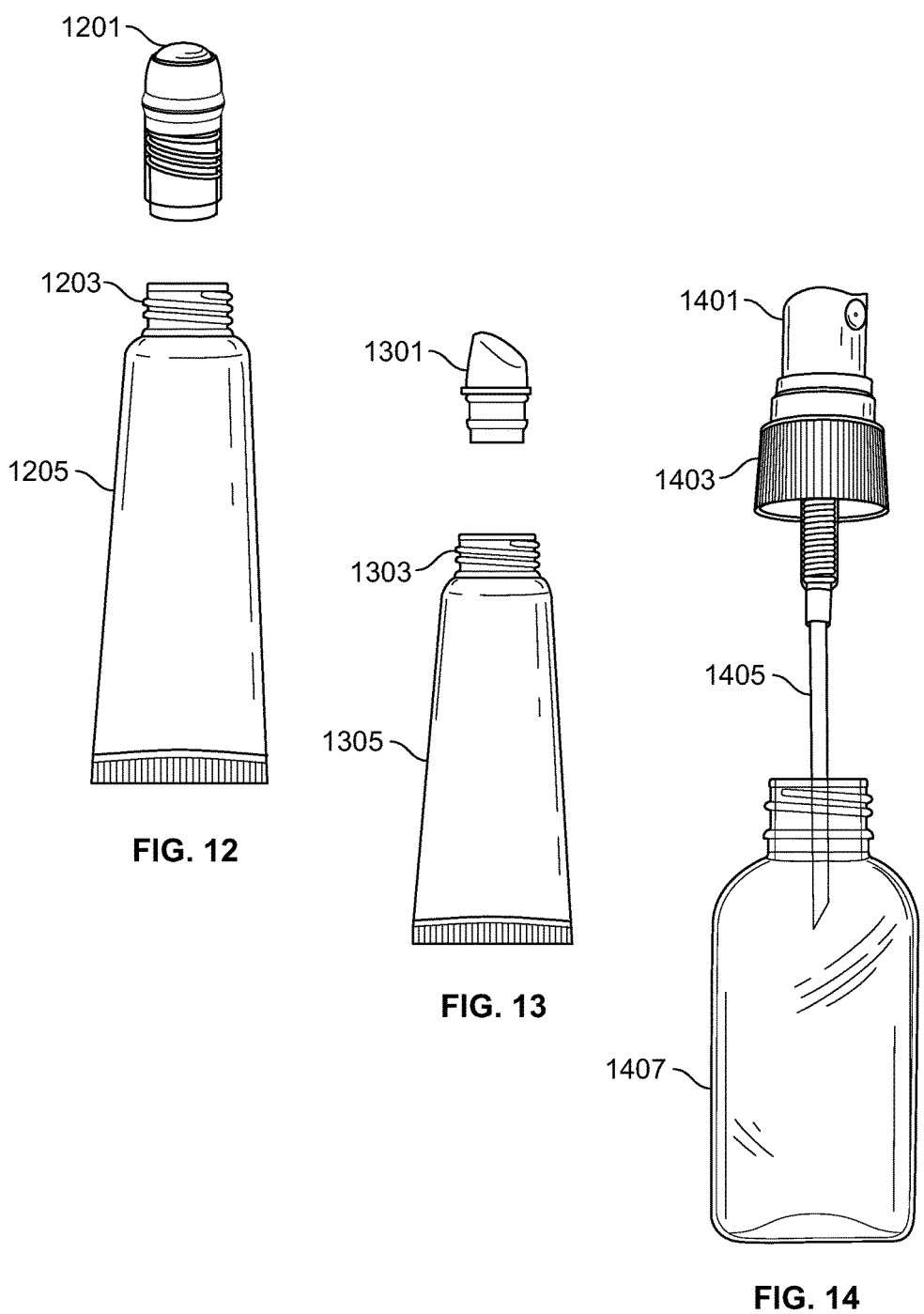
FIG. 12 shows illustrative apparatus for use with the systems and methods of the invention.
FIG. 13 shows illustrative apparatus for use with the systems and methods of the invention.
FIG. 14 shows illustrative apparatus for use with the systems and methods of the invention.

FIG. 12 illustrates yet another applicator for use with the invention. The applicator illustrated in FIG. 12 may include roller ball 1201. Housing including roller ball 1201 may screw onto head 1203. Head 1203 may be located at the top of tube 1205. Tube 1205 may hold solution in accordance with the invention.

When roller ball 1201 is put into contact with a surface, and moved along the surface, roller ball 1201 may rotate, dispensing onto the surface solution held in tube 1205.

FIG. 13 illustrates yet another applicator for use with the invention. The applicator illustrated in FIG. 13 may include applicator tip 1301. Applicator tip 1301 may be attached to housing. The housing may screw onto tube head 1303. Tube head 1303 may be located at the top of tube 1305. Tube 1305 may hold solution in accordance with the invention.

In some embodiments, squeezing tube 1305 may dispense solution into applicator tip 1301.

FIG. 14 illustrates yet another applicator for use with the invention. The applicator illustrated in FIG. 14 may include spray head 1401. Spray head 1401 may be attached to housing 1403. Housing 1403 may support both spray head 1401 and tube 1405. Housing 1403 may screw onto bottle 1407. Bottle 1407 may hold solution in accordance with the invention.

When spray head 1401 is depressed, tube 1405 may draw solution from bottle 1407 and spray the solution out of spray head 1401.

It should be noted that the applicators illustrated in FIGS. 1-14 for use with the invention are for exemplary purposes only. An applicator for use with the invention is not limited in any way to the geometric shape and/or size of the applicators illustrated in FIGS. 1-14. Instead, any suitable shape and/or size of apparatus illustrated in FIGS. 1-14 may be used with the systems and methods of the invention.

Thus, apparatus for applicators and methods for concealing vitiligo have been provided. Persons skilled in the art will appreciate that the present invention can be practiced in embodiments other than the described embodiments, which are presented for purposes of illustration rather than of limitation.

What is claimed is:

1. A method for concealing vitiligo, the method comprising:
    depressing a spring head, the spring head being covered by a covering, wherein depression of the spring head saturates the covering with a solution, the solution being held in an open reservoir and not in a fibrous reservoir and including a bronzer and dihydroxyacetone ("DHA"), the solution comprising a Specific Gravity of between 0.90-1.2, a pH of between 2.5 and 3.7, and a Viscosity (as measured using a viscometer at Spindle #3/100RPM/1 min) of between 4-23 centipoise; and
    guiding the saturated covering over a portion of depigmented skin.

2. The method of claim 1 wherein the spring head is attached to a spring.

3. The method of claim 1 wherein:
the spring head is attached to a spring; and
depression of the spring head in turn depresses the spring.

4. The method of claim 3 wherein the spring is formed from one of high density polyethylene ("HDPE"), low density polyethylene (LDPE), celcon and polypropylene.

5. The method of claim 1 wherein the covering is formed from at least one of polyurethane, neoprene, nylon taffeta and brushed nylon tricot.

6. The method of claim 1 Wherein the spring head comprises a diameter of between about 0.52 inches and about 0.98 inches.

7. The method of claim 1 wherein the spring head comprises a diameter of about 0.52 inches.

8. The method of claim 1 wherein the spring head comprises a diameter of about 0.98 inches.

9. The method of claim 1 wherein the spring head comprises a diameter of about 0.52 inches, the spring head is attached to a spring, depression of the spring, head in turn depresses the spring, and the spring is formed from low density polyethylene (LDPE).

10. The method of claim 1 wherein the spring head comprises a diameter of about 0.98 inches, the spring head is attached to a spring, depression of the spring head in turn depresses the spring, and the spring is formed from high density polyethylene (HDPE).

\* \* \* \* \*

UNITED STATES PATENT AND TRADEMARK OFFICE
CERTIFICATE OF CORRECTION

Page 1 of 1

PATENT NO. : 9,968,532 B2
APPLICATION NO. : 14/143082
DATED : May 15, 2018
INVENTOR(S) : James R. Adelson et al.

It is certified that error appears in the above-identified patent and that said Letters Patent is hereby corrected as shown below:

In the Claims

Claim 6, Line 12, delete "Wherein" and insert --wherein--.
Claim 9, Line 21, delete "spring, head" and insert --spring head--.

Signed and Sealed this
Fourth Day of September, 2018

Andrei Iancu
*Director of the United States Patent and Trademark Office*